United States Patent [19]

Ranade

[11] 4,451,664

[45] May 29, 1984

[54] PROCESS OF MANUFACTURING DIARYL ESTERS OF DICARBOXYLIC ACIDS

[75] Inventor: Gautam R. Ranade, Grand Island, N.Y.

[73] Assignee: Occidental Chemical Corporation, Niagara Falls, N.Y.

[21] Appl. No.: 422,792

[22] Filed: Sep. 24, 1982

[51] Int. Cl.$^3$ .............................................. C07C 67/08
[52] U.S. Cl. ................................. 560/86; 260/455 R; 260/456 P; 560/11; 560/18; 560/37; 560/48; 560/52; 560/73; 560/85; 560/139; 560/142; 560/146; 568/15
[58] Field of Search ........................ 560/11, 18, 37, 52, 560/73, 85, 86, 204, 48, 139, 142, 146; 260/455 R, 456 P; 203/DIG. 6; 568/15

[56] References Cited

U.S. PATENT DOCUMENTS

| | | | |
|---|---|---|---|
| 3,356,712 | 12/1967 | Renckhoff et al. | 560/86 |
| 3,389,164 | 6/1968 | Renckhoff et al. | 560/86 |
| 3,413,336 | 11/1968 | Hulsmann et al. | 560/86 |
| 3,471,549 | 10/1969 | Hulsmann et al. | 560/86 |
| 3,772,389 | 11/1973 | Lowrance | 560/86 |

*Primary Examiner*—Natalie Trousof
*Assistant Examiner*—Vera C. Clarke
*Attorney, Agent, or Firm*—James F. Tao

[57] ABSTRACT

An improved process for preparing diaryl esters of a monohydroxy aromatic compound with dicarboxylic acids is disclosed, in which the esterification reaction is optimized by continuously removing water and/or other by-products of the reaction from the reactor, while supplying to the reactor a make-up amount of the monohydroxy aromatic compound containing no more than about 100 ppm of water. The make-up stream may be obtained by stripping the by-product stream of water and other by-products of the reaction.

10 Claims, 1 Drawing Figure

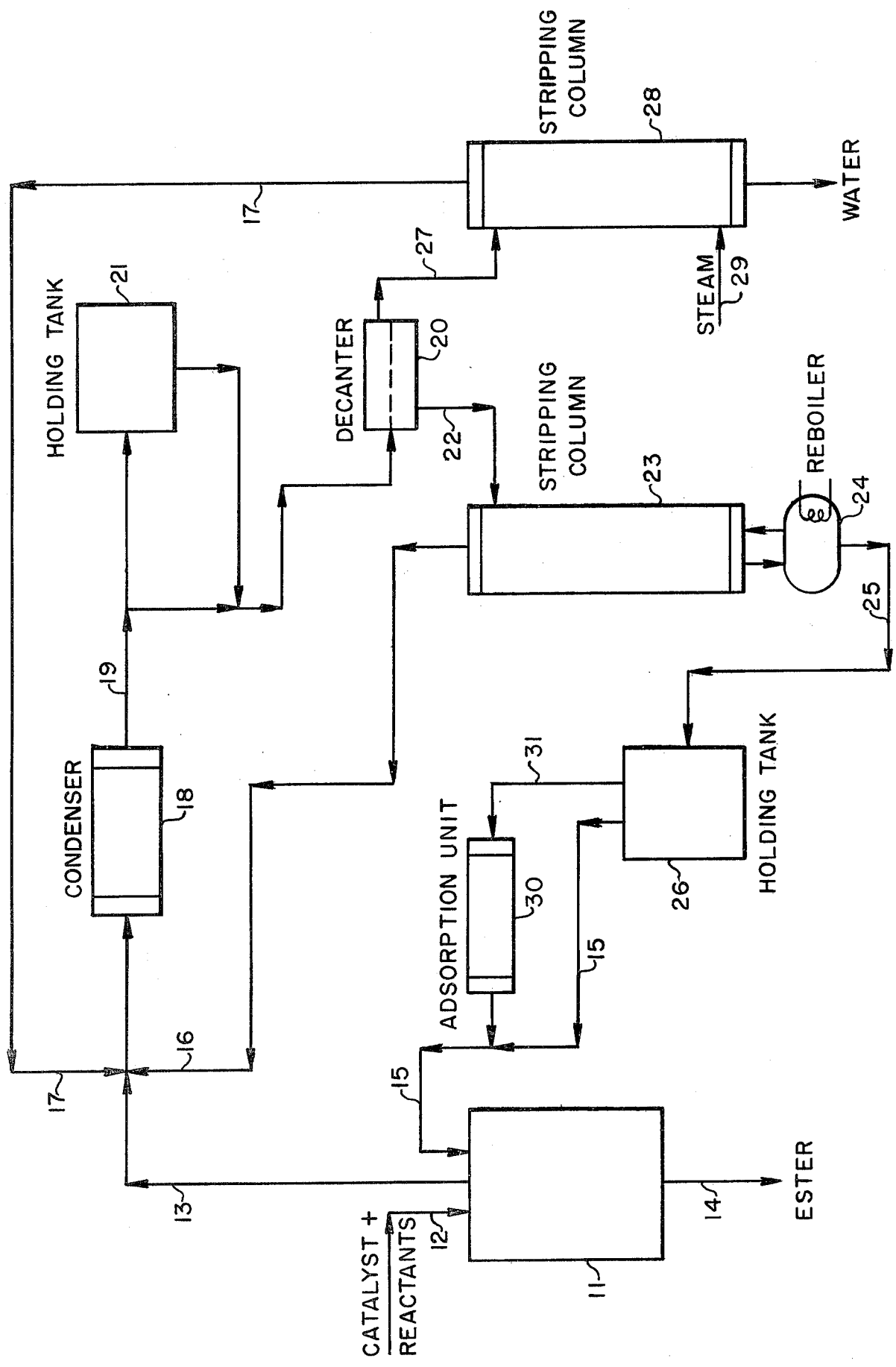

PROCESS OF MANUFACTURING DIARYL ESTERS OF DICARBOXYLIC ACIDS

BACKGROUND OF THE INVENTION AND PRIOR ART STATEMENT

This invention relates to an improved process for making esters. More particularly, the invention relates to an economical and efficient process for making diaryl esters which have very low unreacted acid content.

Linear polyesters which are essentially the product of the reaction of a bisphenol and dicarboxylic acids are important thermoplastic materials due to their excellent performance at high temperatures. It is known to produce such linear polyesters by first reacting at least one dicarboxylic acid with a monohydroxy aromatic compound to form a diaryl ester of the dicarboxylic acid, and then carry out a transesterification polymerization between the diaryl ester and a bisphenol. See, e.g. British Pat. No. 924,607 and U.S. Pat. Nos. 4,255,555 and 4,319,017. However, those references are primarily concerned with transesterification reaction for preparing the linear polyesters.

Significant commercial interest in recent years has developed in the field of phenolic esters of aromatic dicarboxylic acids, such as diphenyl isophthalate and diphenyl terephthalate, due to their use in many processes. For example, mixtures of diphenyl isophthalate and diphenyl terephthalate can be reacted by melt polycondensation with 4,4-(1-methyl-ethylene)-bis(phenol) to produce aromatic polyesters or polyarylates. Diphenyl phthalates can also be reacted with primary amines in a solvent to make polyamides. Likewise, 3,3' diaminobenzidene may be condensed with various diphenyl esters to form polybenzimidazoles.

The prior art processes for preparing the diaryl esters have a number of disadvantages. To obtain a linear polyester which has outstanding performance at high temperatures as well as a product of diminished color, a relatively high molecular weight polymer must be obtained. However, unreacted acids in the diaryl ester, even in relatively low concentrations, is detrimental to the polymerization reaction and to the obtaining of a polyester having relatively high molecular weight. It is believed that unreacted acid in the diaryl ester adversely affects the catalyst used in the polymerization reaction. The unreacted acid content in the ester must be very low, in the hundreds parts per million range (at an acid number of less than about 0.5), in order to obtain a polyester product of high quality.

Although unreacted acid in the ester product can be removed by separation processes such as distillation means, such separation is difficult and expensive at the low acid concentrations involved. More importantly, when a mixture of acids are used to obtain a specific mix of esters, the separation of the unreacted acids may disturb the relative ratios of the esters in the product stream. Thus, there are advantages in limiting the unreacted acid content in the ester product stream by driving the esterification reaction towards completion as much as possible. Generally, I have found that the esterification reaction would have to be substantially over 90% completion in order to obtain an ester product of sufficient purity for subsequent polymerization reaction. A degree of esterification of at least about 95% is preferred. In the past, such high degrees of completion of the esterification reaction have been accomplished by employing relatively high reaction temperatures and/or long reaction times. However, such high temperatures and/or long reaction times degrade the ester product and produce colored by-products which greatly diminish the value of the esters so produced.

Other prior art found in the search includes U.S. Pat. Nos. 3,039,980; 3,068,206; 3,109,831; 3,376,353; 3,418,286; 4,146,729; and 4,254,246. None of these patents are believed to be particularly relevant to the present invention.

It is therefore, an object of the invention to provide an improved process for making diaryl esters of dicarboxylic acids.

It is another objection of the present invention to provide an economical process for making diaryl esters of high quality, which can be subsequently polymerized to a polymer of high molecular weight and low discoloration.

These and other objects of the invention can be gathered from the following disclosure.

SUMMARY OF THE INVENTION

In accordance with the present invention, there is provided a process for the esterification of at least one dicarboxylic acid with a monohydroxy aromatic compound, in which the dicarboxylic acid is represented by the formula

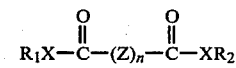

wherein X is oxygen or sulfur, Z is alkylene, —Ar— or —Ar—Y—Ar— wherein Ar is aromatic, Y is alkylene of 1 to 10 carbon atoms, haloalkylene, —O—, —SO—, —SO$_2$—, —SO$_3$—, —CO—,

or GN=, and G is alkyl, haloalkyl, aryl, haloaryl, alkylaryl, haloalkylaryl, arylalkyl, haloarylalkyl, cycloalkyl and halocycloalkyl, n is 0 or 1, and R$_1$ and R$_2$ are independently selected from the group consisting of hydrogen and lower alkyl. The esterification reaction is carried out at a temperature between about 220° to about 300° C., preferably in the presence of a catalyst while continuously removing a by-product of the esterification reaction comprising water and/or lower alkyl alcohol(s) in admixture with the monohydroxy aromatic compound from the reactor, and supplying to the reactor a make-up amount of the monohydroxy aromatic compound. Surprisingly, the applicant has found that the esterification reaction can be conducted at a relatively low temperature and yet achieve high conversion rates over short reaction times by using as the make-up material a monohydroxy aromatic compound containing no more than about 100 parts per million (ppm) of water. Preferably, the monohydroxy aromatic compound used as the make-up stream is recovered from the by-product stream removed from the reactor. It is important that in recycling such monohydroxy aromatic compound, the water content be reduced to no more than about 100 ppm, and most preferably to no more than about 50 ppm. Advantageously, the water content in the recycled monohydroxy aromatic compound can be reduced by a stripping column, optionally, in conjunction with other water separation means such as an adsorption unit.

BRIEF DESCRIPTION OF THE DRAWING

In the drawing, a simple reactor system for carrying out the esterification reaction in accordance with the present invention is shown. A stirred reactor vessel 11, which is preferably equipped with a heating means and a temperature sensing means (both not shown), has an inlet conduit 12 for admitting the reactants and catalyst into the reactor. An outlet conduit 13 is fitted on the reactor for the removal of by-products of the esterification reaction, which is in admixture with the monohydroxy aromatic compound. The ester product from the reactor is removed via line 14. The remainder of the reactor system is concerned with the purification of the monohydroxy aromatic compound removed from the reactor via conduit 13 and returned to the reactor via line 15.

The by-product stream removed from the reactor 11 is passed via conduit 13, together with the overhead streams 16 and 17 from the two stripping columns to be described below, through a condenser 18. The condensed by-product stream 19 is passed into a decanter 20 in which a phase separation occurs. Optionally, the condensed by-product stream 19 may be first passed into a holding tank 21 for storage prior to entry into decanter 20. From decanter 20, a stream 22, which is rich in the monohydroxy aromatic compound, is passed into the top of stripping column 23. In stripping column 23, the monohydroxy aromatic compound is stripped of water and other by-products of the esterification reaction. A re-boiler 24 supplies energy to the stripping column 23. The bottoms stream 25 of the stripping column 23 is purified monohydroxy aromatic compound containing very little water and it is passed into a holding tank 26. The overhead stream 16 from the stripping column 23, which is relatively rich in water, is combined with the by-product stream from the reactor in conduit 13 and passed through the condenser 18. The stream 27 from the decanter 20, which is relatively rich in water and other by-products of the esterification reaction, is passed into the top of a stripping column 28 and there stripped by steam 29. The monohydroxy aromatic compound present in stream 27 is recovered in stripping column 28 as overhead stream 17, which is combined with overhead stream 16 and the by-product stream 13 from the reactor. The bottoms from the stripping column 28 is essentially water and is passed to waste disposal.

The essentially pure monohydroxy aromatic compound stored in holding tank 26 may be recycled to the reactor 11 via line 15 or, optionally, it may be further purified by other water separation means such as by passing through an adsorption means 30 via conduit 31.

DETAILED DESCRIPTION OF THE INVENTION

As indicated above, the present invention provides an improved process for preparing diaryl esters, which are useful in the preparation of linear polyesters, by the reaction of at least one dicarboxylic acid or its ester with a monohydroxy aromatic compound. The dicarboxylic acids which are useful in the process of the invention are known and they can be represented by the formula:

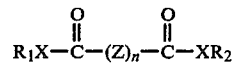

in which X is oxygen or sulfur, Z is alkylene, —Ar— or —Ar—Y—Ar— where Ar is aromatic, Y is alkylene of 1 to 10 carbon atoms, haloalkylene, —O—, —SO—, —SO$_2$—, —SO$_3$—, —CO—,

or GN=, and G is alkyl, haloalkyl, aryl, haloaryl, alkylaryl, haloalkylaryl, arylalkyl, haloarylalkyl, cycloalkyl and halocycloalkyl, n is 0 or 1, and R$_1$ and R$_2$ are independently selected from the group consisting of hydrogen and lower alkyl. Examples of aromatic and aliphatic dicarboxylic acids are disclosed in U.S. Pat. No. 4,126,602, and they include: aromatic dicarboxylic acids such as phthalic acid, isophthalic acid, terephthalic acid, bis(4-carboxyl)-diphenyl, bis(4-carboxyphenyl)-ether, bis(4-carboxyphenyl)-sulfone, bis(4-carboxyphenyl-carbonyl, bis(4-carboxyphenyl)-methane, bis(4-carboxyphenyl)-dichloromethane, 1,2- and 1,1-bis(4-carboxyphenyl)-ethane, 1,2- and 2,2-bis(4-carboxyphenyl)-propane, 1,2- and 2,2-bis(3-carboxyphenyl)-propane, 2,2-bis(4-carboxyphenyl)-1,1-dimethyl propane, 1,1- and 2,2-bis(4-carboxyphenyl)-butane, 1,1- and 2,2-bis(4-carboxyphenyl-pentane, 3,3-bis-(4-carboxyphenyl)-heptane, 3,3-bis(3-carboxyphenyl)-heptane; and aliphatic acids such as oxalic acid, adipic acid, succinic acid, malonic acid, sebacic acid, glutaric acid, azelaic, suberic acid and the like. Isophthalic acid and terephthalic acid are the preferred dicarboxylic acids for use in the process of the present invention, due to their easy availability and low cost. More preferably, the dicarboxylic acid employed in the esterification reaction comprises a mixture of about 60 to about 100 mole percent isophthalic acid and about 40 to about 0 mole percent terepthalic acid. Most preferably, the dicarboxylic acid component is made of a mixture of about 75 to about 85 mole percent isophthalic acid and about 25 to about 15 mole percent terephthalic acid.

The monohydroxy aromatic compounds for use in the process in the present invention is also known. Generally, they may be of the benzene or naphthalene series containing 6 to 29 carbon atoms. Examples of such monohydroxy aromatic compounds include phenol, o-, m-, or p-cresol, xylenol, a halophenol such as p-chlorophenol, 3,5-cibromophenol, a nitrophenol such as o-, m- or p-nitrophenol, 1-naphthol, 2-naphthol, 1-hydroxy-4-methyl naphthlene, and the like.

The dicarboxylic acid useful in the reaction of the present process include both aliphatic and aromatic acids as well as their respective esters. The rate of conversion may be enhanced when using mixtures of the acids or esters by increasing the proportions of the more soluble acid or ester in monohydroxy aromatic compounds over the less soluble acid or ester. In determining the exact proportion of acids to be used, consideration should be given to the properties of the esters produced and the effect they may have on the linear polyesters produced therefrom. When using mixtures of isophthalic and terephthalic acids, normally the isophthalic acid content will be increased up to the point where no significant change in polymer properties or processing characteristics are observed.

A molar excess of monohydroxy aromatic compound is preferably used in the reaction with the dicarboxylic acid to facilitate the completion of the esterification reaction. Although a molar ratio of the monohydroxy aromatic compound to the dicarboxylic acid of about 2:1 may be used, it is preferred that such molar ratio be from about 3:1 to about 10:1. More preferably, such molar ratio employed should be from about 4:1 to about 8:1.

The temperature to be employed in esterification process of the invention may be varied. Generally, temperatures should be between about 220° to 300° C. Most preferably, the temperature should be between about 235° C. to about 255° C. The pressure employed in the present process is determined by the temperature, the particular reactants employed, and other operating conditions. Generally, the pressure in the reaction vessel is substantially below 100 psig. Due to the relative molecular weights of water and the monohydroxy aromatic compound and their vapor pressures, a small amount of water in the reactants may cause the initial pressure in the reactor to be somewhat higher than indicated herein.

As indicated above, a catalyst is preferably used in the esterification reaction. These catalysts are known in the art. See, e.g., U.S. Pat. No. 4,124,566. Examples of the catalysts are elemental metals such as sodium, potassium, lithium, calcium, magnesium, barium, tin, strontium, zinc, iron, aluminum, cobalt, lead, nickel titanium, magnesium, antimony or arsenic, and compounds of these metals such as their oxides, hydrides, hydroxides, halides, inorganic acid salts, organic acid salts, complex salts, double salts, alcoholates, or phenolates. Of these, titanium compounds such as titanium tetrabutoxide, titanium oxalate or titanium oxide, tin compounds such as dibutyltin oxide, antimony compounds such as antimony trioxide, and lead compounds such as lead are preferred. I have found that organic titanium compounds, such as certain aliphatic esters of ortho titanic acid, are especially effective catalysts. Examples of aliphatic esters of ortho titanic acids include tetrabutyl titanate, tetraisopropyl titanate or tetraoctylene glycol titanate. Some of these organic titanium catalysts are available from the duPont Company under its trademark Tyzor. The amount of the catalyst to be used is also known in the art, and it is usually between about 0.001 to about 5 mole percent based on the amount of the dicarboxylic acid employed.

The esterification reaction carried out in the reactor 11 produces water and other by-products. To facilitate the completion of the esterification reaction, water and other by-products must be essentially continuously removed from the reactor. Since the water content in reactor 11 must be kept as low as possible, the amount of the monohydroxy aromatic compound removed with water and other by-products is relatively large. Clearly, this large amount of the monohydroxy aromatic compound must be recovered and recycled to make the process economically feasible. It has now been discovered that the water content in this recycled monohydroxy aromatic compound stream (line 15 in the drawing) must be kept below about 100 parts per million (ppm), and most preferably below about 50 ppm. In addition, the present invention discloses a process by which the recycled monohydroxy aromatic compound stream may be so purified.

In the prior art esterification processes, the reaction is generally driven to substantial completion by the use of high temperatures and/or long reaction times. Such high reaction temperatures and/or long reaction times detrimentally affect the esters so produced, and introduce discoloration to the ester product which is carried over and further magnified during the subsequent polymerization process. Such a discolored product is extremely undesirable and of substantially less value than a colorless or clear product. In may two co-pending applications concurrently filed with the present application, the disclosure of which are incorporated herein by reference, two methods for optimizing the esterification reaction are disclosed: In one case, the esterification reaction is conducted at relatively lower temperatures and yet achieve high conversion rates over short reaction times by the use of reaction temperature which is increased during the course during the course of the esterification reaction according to a predetermined pattern; and in the other case, the esterification reaction is optimized by controlling the rate of removal of water and other by-products of the reaction by varying the reflux ratio in the distillation means used for the removal during the course of the esterification reaction. As indicated above, it has now been discovered that the esterification reaction can be economically and efficiently optimized by maintaining the water content in the reactor at extremely low levels. Such low water content in the reactor is maintained by the substantially complete removal of water and other reaction by-products from the reactor together with a large amount of the monohydroxy aromatic compound reactant, and then purifying the monohydroxy aromatic compound so removed from the reactor to reduce the water content therein to less than about 100 ppm before recycling the monohydroxy aromatic compound back into the reactor.

It is to be understood that the process of varying the reaction temperature during the course of esterification reaction according to a predetermined pattern, as disclosed in the above mentioned copending application, may be employed in conjunction with the process of the present invention.

It is critical that the water content of the recycled monohydroxy aromatic compound stream be maintained at below about 100 ppm. Such low water content will permit completion of the esterification reaction in a short period using moderate temperatures. At substantially higher water contents, such as 1000 ppm or more, the esterification reaction is more difficult to complete and usually will be accomplished by the use of higher temperatures or reaction periods, both of which leads to undesirable product discoloration and degradation.

A preferred embodiment for carrying out the process of the present invention is shown in the drawing. The reactants charged to the stirred reactor may be a mixture of isophthalic acid and terephthalic acid together with phenol. The catalyst may be, say, antimony oxide. The ester product stream 14 comprises a mixture of diphenyl isophthalate and diphenyl terephthalate. The by-product stream removed via conduit 13 is essentially at the temperature inside the reactor, and it is composed of water and alcoholic by-products of the reaction as well as phenol. This by-product stream is then combined with overhead streams 16 and 17 and passed through the condenser 18 to liquify the vapors. The condensed by-product stream 19 should be at a suitable temperature, say at least 60° C., so that the phenol therein would not be solidified. After phase separation in decanter 20, the phenol-rich stream 22 is stripped of its water content in the stripping column 23. Due to the phase relationship between phenol and water, relatively few theoretical plates in the stripping column 23 are necessary to substantially completely remove the water in that stream. The phenol value in the water-rich stream 27 from decanter 20 can be recovered by stripping in column 28. The purified phenol so recovered (stream 25) is ready for recycling into the reactor 11. Optionally, the water content of stream 25 may be further reduced by separation means such as an adsorption unit 30.

By maintaining the water content in the recycled phenol stream 15 to below about 100 ppm, and more preferably below 50 ppm, I have found that esterification reaction can be carried out at moderate temperatures in 2-3 hours and yet obtain a degree of esterification of about 95% or higher. The process of the invention is also energy efficient in that the stripping column 23 can be operated at relatively low reflux ratios, for example, at a reflux ratio of between 1-5, and more preferably at a reflux ratio between 2-3.

The present application is being concurrently filed with applicant's co-pending applications Ser. Nos. 422,793 and 422,794, both for Process of Manufacturing Diaryl Esters of Dicarboxylic Acids, the disclosures of which are incorporated herein by reference.

The invention has been described with reference to particular and preferred embodiments thereof. It is to be understood that various changes and modifications can be made without departing from the spirit and scope of the invention.

What is claimed is:

1. In a process for preparing esters which comprises reacting a monohydroxy aromatic compound with at least one dicarboxylic acid in a reactor having a distillation means, said acid being represented by the formula:

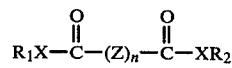

wherein X is oxygen or sulfur, Z is alkylene, —Ar— or —Ar—Y—Ar— wherein Ar is aromatic, Y is alkylene of 1 to 10 carbon atoms, haloalkylene, —O—, —SO—, —SO$_2$—, —SO$_3$—, —CO—,

or GN=, and G is alkyl, haloalkyl, aryl, haloaryl, alkylaryl, haloalkylaryl, arylalkyl, haloarylalkyl, cycloalkyl and halocycloalkyl, n is 0 or 1, and R$_1$ and R$_2$ are independently selected from the group consisting of hydrogen and lower alkyl, said reaction being conducted at a temperature between about 220° to about 300° C., continuously removing a by-product of said reaction comprising water and/or lower alkyl alcohol(s) in admixture with said monohydroxy aromatic compound from said reactor through said distillation means, and supplying to said reactor a make-up amount of said monohydroxy aromatic compound, the improvement which comprises using as said make-up material a monohydroxy aromatic compound containing no more than about 100 ppm of water.

2. A process according to claim 1 further comprising removing said water and/or lower alkyl alcohols from said by-product stream and returning the remaining monohydroxy aromatic compound as the make-up material to said reactor.

3. A process according to claim 2 wherein said water and/or lower alkyl alcohols are removed by a stripping column.

4. A process according to claim 3 wherein said dicarboxylic acid comprises isophthalic acid, terephthalic acid, and mixtures of isophthalic and terephthalic acids.

5. A process according to claim 3 wherein said monohydroxy aromatic compound is of the benzene or naphthalene series containing from 6 to about 20 carbon atoms.

6. A process according to claim 3 wherein said monohydroxy aromatic compound is phenol, a halo-phenol, or a nitro-phenol.

7. A process according to claim 3 wherein said reaction is conducted in the presence of a catalyst.

8. A process according to claim 7 wherein said catalyst is antimony oxide or an aliphatic ester of ortho titanic acid.

9. A process according to claim 3 wherein the water content of said by-product stream is further reduced by an adsorption means.

10. A process according to claim 3 wherein the water content in said make-up material is no more than about 50 ppm.

* * * * *